United States Patent
Wang et al.

(10) Patent No.: US 11,680,290 B2
(45) Date of Patent: Jun. 20, 2023

(54) EFFICIENT METHODS AND COMPOSITIONS FOR MULTIPLEX TARGET AMPLIFICATION PCR

(71) Applicant: Chapter Diagnostics, Inc., Menlo Park, CA (US)

(72) Inventors: Chunlin Wang, Menlo Park, CA (US); Zhihai Ma, Mountain View, CA (US); Baback Gharizadeh, Menlo Park, CA (US)

(73) Assignee: Chapter Diagnostics, Inc., Menlo Park, CA (US)

( * ) Notice: Subject to any disclaimer, the term of this patent is extended or adjusted under 35 U.S.C. 154(b) by 85 days.

(21) Appl. No.: 16/720,823

(22) Filed: Dec. 19, 2019

(65) Prior Publication Data

US 2021/0189457 A1  Jun. 24, 2021

(51) Int. Cl.
  *C12Q 1/686* (2018.01)
  *C12Q 1/6874* (2018.01)
  *C12Q 1/6855* (2018.01)

(52) U.S. Cl.
  CPC .......... *C12Q 1/686* (2013.01); *C12Q 1/6855* (2013.01); *C12Q 1/6874* (2013.01); *C12Q 2600/156* (2013.01); *C12Q 2600/16* (2013.01)

(58) Field of Classification Search
  None
  See application file for complete search history.

(56) References Cited

U.S. PATENT DOCUMENTS

2019/0002872 A1*  1/2019  Andersen ............ C12Q 1/6806

\* cited by examiner

*Primary Examiner* — Teresa E Strzelecka
(74) *Attorney, Agent, or Firm* — Butler Snow LLP

(57) ABSTRACT

The present disclosure relates to methods of enzymatic treatment of double-stranded PCR amplified products for eliminating or minimizing primer-dimers in multiplex PCR reactions and for the efficient ligation of adapters. The present disclosure relates to methods and compositions that allow more efficient highly multiplex target amplification compared to conventional methods, compositions and kits by minimizing laboratory steps, eliminating primer-dimers and increasing the efficiency of adapter ligation. The disclosed methods use multiple target-specific primers for specific and selective amplification of targets in a subject's genome. The disclosed methods can be used for numerous downstream procedures and analysis, including DNA sequencing.

20 Claims, 12 Drawing Sheets

Specification includes a Sequence Listing.

Figure 8

EGFR: 114 bp (chr7:55241641-55241754, hg19) with adapter sequence

Illumina P5 adapter sequence

Sequencing primer →

AATGATACGGCGACCACCGAGATCTACACAATACGCCACACTCTTTCCCTACACGACGCTCTTCCGATCTGAAGCTCCCAACCAAGCTCTCTTGAGGATCTTGAAGGAAACTGAATTCAAAAAGATCAA
AGTGCTGGGTCCGGTGCGTTCGGCACGGTGTATAAGGTAAGGTCCCTGGCACAGAGATCGGAAGAGCACACGTCTGAACTCCAGTCACGCGTATTATCTCGTATGCCGTCTTCTGCTTG

EGFR gene sequence                                    Illumina P7 adapter sequence Reverse complement sequence Illumina P7 adapter sequence Sequencing primer →

CAAGCAGAAGACGGCATACGAGATAATACGCCGTGACTGGAGTTCAGACGTGTGCTCTTCCGATCTCTGTGCCAGGGACCTTACCTTATACACGTGCCGAACGCACCGGAGCCCAGCACTTTG
ATCTTTTTGAATTCAGTTCCTTCAAGAGATCTTCAAGAGAGCTTGGTTGGGAGCTTCAGATCGGAAGAGCGTCGTGTAGATCGGCCGTATTGTGTAGATCGTCGGTCGTCCGTATCATT

EGFR gene sequence                                    Illumina P5 adapter sequence TP53: 119 bp (chr17:7577492-7577610, hg19) with adapter sequence KIT_4 156bp 156 bp (chr4:55599221-55599376, hg19) with adapter sequence

EFFICIENT METHODS AND COMPOSITIONS FOR MULTIPLEX TARGET AMPLIFICATION PCR

BACKGROUND OF THE INVENTION

Rapid and accurate identification of genetic variants contributing to disease, drug response or adverse drug effects is crucial for the diagnosis, individualized treatment, companion diagnostics and prognosis of patients. Many cancers and congenital or inherited disorders are complex diseases, which may be linked to multiple genes and may involve heterozygous mutations. Moreover, these mutations may exist in a small quantity in a given sample.

Targeted gene sequencing is an effective approach for analyzing specific mutations and genetic changes in a sample. Target gene sequencing allows a focus deeper upon a set of selected genes or gene regions that are known, or suspected, to associate with a particular disease. Multiple genes can be analyzed in parallel across the genome, thereby reducing time and cost. Targeted gene sequencing also generates a more detailed data set for the genes of interest, providing high sensitivity, specificity and in-depth coverage, allowing for easier gene analysis and the detection of rare gene variants.

Moreover, because the majority of known disease-causing mutations occur in the coding region of genes, concentrating the focus for a sequence analysis on a panel of genes relevant to a particular disease is more practical. Targeting, capturing, and sequencing the genomic regions of interest is especially valuable in clinical settings, so that each target can be analyzed with greater depth and large number of specific gene panels and high sample numbers can be analyzed simultaneously. As such, there remains a great need to design applications where a focus on specific genomic intervals or gene sets is required.

While whole genome sequencing is becoming more cost-effective and more practical for many indications, a focused target-specific panel continues to offer the advantages of better coverage of targeted regions and a greater ability to detect multiple variant types (including CNVs and complicated genomic rearrangements) at substantially lower costs, higher throughput, simpler bioinformatics analysis, and more focused testing. Such focused target-specific panels obviate the need to deal with the secondary/incidental findings that otherwise inevitably arise with whole genome sequencing. Furthermore, targeted sequencing of specific regions of interest in a large number of samples is much more cost-effective in characterizing a disease state than sequencing the whole genomes of fewer individuals. Wider coverage of specific targets and deeper sequencing of enriched targets allows a broader dynamic range in allele frequencies and detection of minority sequences and low frequency variations for disease evaluation, treatment and prognosis. An efficient and specific target enrichment method allows more efficient targeted sequencing. The important parameters for target enrichment are: (i) sensitivity; (ii) specificity; (iii) uniformity; (iv) reproducibility; (v) cost; (vi) ease of use; and (vii) the amount of DNA required per experiment.

The human genome contains approximately 3 billion bases, about 21,000 coding genes and over 220,000 exons. The exons represent around 1-2% of the genome, and there are nine exons per gene on an average scale with an average exon size of 170 nucleotides. Next generation sequencing (NGS) is an important tool for analyzing the genome, has a higher sensitivity than Sanger sequencing, allowing the detection of mutations from a sample containing just a few cells. It can be utilized to detect multiple sequence variations such as single and multi-nucleotide variants, insertions, deletions and gene copy number variations in DNA and RNA. NGS can also be utilized to analyze gene expression levels by measuring quantitatively the levels of mRNA, microRNA and factors affecting them like gene promoter methylation. Currently there are three types of NGS for sequencing DNA: (a) whole-genome sequencing (WGS); (b) whole-exome sequencing (WES); and (c) targeted sequencing. WGS covers and analyzes the entire genomic content of an individual, while WES covers only the protein-coding regions of the genome. Targeted sequencing, in contrast, focuses on a set of genes or specific regions of the genome that are linked by common pathological mechanisms or known clinical phenotype.

Remarkably, NGS is revolutionizing molecular characterization of inherited diseases and cancers both for discovery of driver mutations and the routine screening of genomic aberrations. Because of a wide range of different applications, NGS has covered many fields of life sciences and is significantly impacting medical genetics, both in research and diagnostics. Isolating high-priority segments of the genomes immensely enhances the outcome in clinical, diagnostic and research settings. Using NGS to focus on particular regions of interest, however, requires enrichment of relevant target regions. Notably, target enrichment allows increased coverage of target regions and specific regions of interest, facilitating multiplexing of samples and simplifying sequence read data analysis. Fundamental advantages of target enrichment in genomic assays include enrichment factor, coverage or read depth, uniformity or evenness of coverage across the target region of interest, reproducibility, specificity that is on-target/off-target ratio of sequence reads, required input DNA amount and overall cost per target base of useful sequence data.

PCR-based target enrichment methods are relatively fast, require few steps and little input DNA, and as a result are more suitable for samples containing low amounts of input DNA, such as FFPE, cfDNA and ctDNA. The specificity of PCR for target enrichment of regions of interest is significantly influenced by the number of primers in the reaction and primer characteristics such as G-C content and presence of variations in target regions might interfere with optimal primer hybridization, causing amplification failure of certain sequences also known as allele drop-out. Amplicon size and coverage are important considerations for PCR based target enrichment to generate even and uniform coverage.

Multiplex amplification of target nucleic acid sequences allows a great number of applications in a single polymerase chain (PCR) reaction. The advantage of using multiple target-specific primers in a single PCR reaction is that doing so allows multiplex amplification of selective targets in an efficient manner, saving time, lowering cost and reducing labor as well as increasing throughput. However, increasing the number of oligonucleotide primers in a reaction may introduce primer cross-reactivity and the formation of amplification artifacts such as primer-dimers or non-specific priming leading to non-specific amplification products. Furthermore, some nucleic acid targets may not be amplified due to this cross-reactivity, causing nucleic acid target dropouts. These amplification artifacts may overly consume amplification components and reagents such as dNTPs and DNA polymerase, affecting the overall efficiency and quality of the amplification reaction. These artifacts from highly multiplex amplifications may also affect the downstream procedures such as sample preparation for next-generation sequencing. In such circumstances, the amplification of non-specific amplifications or artifacts can be carried to the downstream steps such as next-generation sequencing read results, generating overly dominant non-informative sequencing reads.

Multiplex amplification can amplify multiple targets of interest in one reaction and advantageously increase the number of target regions that can be amplified in a single reaction starting from limited amounts of DNA where hundreds to thousands of target regions can be amplified simultaneously for sequencing. Selective multiplex amplification has a wide range of applications in clinical and research settings and can be used for mutation detection and analysis, single nucleotide polymorphisms (SNPs), microbial and viral detection, deletions and insertions, genotyping, copy number variations (CNV), epigenetic and methylation analysis, gene expression, and transcriptome analysis. These applications can be used for diagnostics, prognosis and the treatment of disease.

As the number of nucleic acid target regions for selective amplification increase, however, proportionally more primers need to be introduced into the reaction. Higher primer numbers and concentrations in a single test reaction may increase the amplification artifacts such as primer-dimers, non-specific amplifications, super-amplicons, and can cause failed amplification due to interference between primers, each of which can negatively impact downstream steps. A common approach to avoid or minimize these amplification artifacts is the use of commercial or in-house software packages to design primers for multiplex amplification assays to avoid or lower the chance of primer-dimer formations and non-specific priming. This can be done by: (1) using stringent design considerations to design target specific primers to mitigate primer interactions; and (2) grouping primers into optimal subsets of non-overlapping pools to avoid artifacts.

Such efforts, however, do not completely solve the aforementioned issues and, as such, there is a great need for methods or compositions for highly multiplex amplification of target-specific sequences without or minimal amplification artifacts such as primer-dimers and non-specific amplification products as well as eliminating or minimizing primer grouping for separate test reactions, which adds extra steps.

SUMMARY OF THE INVENTION

In some embodiments, the present disclosure relates to methods, compositions and kits for multiplex target amplification and target enrichment prior to downstream analysis such as next-generation sequencing. In certain embodiments, the present disclosure relates to a method comprising the step of using a plurality of target-specific primers to perform target enrichment amplification in a DNA or RNA sample, wherein the amplification is conducted under optimal conditions in the presence of amplification reagents comprising polymerase and dNTPs. In various embodiments, the method further comprises the step of converting mRNA in a sample to cDNA. In some embodiments, the target-specific primers of the method comprise a target-specific sequence at the 3'-end and an auxiliary sequence at the 5'-end, wherein the auxiliary sequence is configured to allow digestion of PCR product around the methylated site with a proper restriction enzyme.

In some embodiments, the disclosure is directed to a method comprising the steps of: (1) in a test reaction, hybridizing two or more target-specific primers to nucleic acid target sequences, wherein the target-specific primers comprise a methylated universal auxiliary portion with a methylation-dependent endonuclease restriction enzyme recognition site and a target-specific portion configured to target nucleic acid target sequences in the sample; (2) subjecting the test reaction to amplification under optimal amplification conditions to produce an amplified product comprising an amplicon; (3) subjecting the amplified product to digestion with a methylation-dependent endonuclease restriction enzyme to form a digestion product, wherein the digestion product comprises amplicons comprising sticky ends (i.e., unpaired nucleotides) on each end of the strands; (4) performing size selection purification on the digestion product for removal of digested primer-dimers and unused primers to form digested amplicons comprising dsDNA; (5) ligating universal adapters to dsDNA from the digested amplicons to form a ligation product, wherein the ligation universal adapters comprise a universal sequence portion and sticky ends; (6) subjecting the ligation product to amplification with barcoded universal primers complementary to a sequence on the ligating universal adapters to form a final amplification product; and (7) quantifying the final amplification product for next-generation sequencing.

In some embodiments, the disclosure is directed to a method comprising the steps of: (1) in a test reaction, hybridizing two or more target-specific primers to nucleic acid target sequences, wherein the target-specific primers comprise a complementary universal auxiliary portion at the 5'-end and a target-specific portion configured to target the nucleic acid target sequences in the sample; (2) subjecting the test reaction to a first amplification by universal auxiliary primers under optimal amplification conditions to form an amplified product; (3) subjecting a portion of the amplified product to a second amplification using a methylated universal auxiliary primer to form a second amplified product, wherein the methylated universal auxiliary primer comprises a restriction enzyme recognition sequence; (4) subjecting the second amplified product to digestion with a methylation-dependent endonuclease restriction enzyme to form a digestion product comprising amplicons comprising sticky ends on each end of the strands; (5) performing size selection purification on the digestion product to remove digested primer-dimers and unused primers to form digested amplicons comprising dsDNA; (6) ligating universal adapters to dsDNA from the digested amplicons to form a ligated product, wherein the ligating universal adaptors comprise complementary sticky ends and a universal sequence portion; (7) subjecting the ligated product to a third amplification using barcoded universal primers complementary to sequences on the ligating universal adapters; and (8) quantifying the final amplification product for next-generation sequencing.

In some embodiments, the disclosed methods comprise the steps of: (1) annealing at least 10, 20, 100, 500, 1,000, 2,500, 5,000, 10,000, 25,000, 50,000, 80,000, 100,000, 150,000 or greater target nucleic acid sequences to target-specific primers, wherein the target-specific primers comprise both forward and reverse primers; and (2) generating target amplification products using primer extension, wherein the target amplification products comprise different sized amplicons. In some embodiments, the disclosed methods further comprise the step of determining the presence or absence of at least one target amplification product. In some embodiments, the disclosed methods further comprise the step of determining the sequence of at least one target amplification product. In some embodiments, the disclosed methods comprise the step of using at least 10, 20, 100, 500, 1,000, 2,500, 5,000, 10,000, 25,000, 50,000, 80,000, 100,000, 150,000 or more forward primers and reverse primers, wherein each forward primer and reverse primer is directed to hybridize to a specific target nucleic acid sequence. In certain embodiments, the disclosed methods further comprise the step of performing RNA analysis for RNA expression measurements both in a control sample and a subject sample by comparison of control expression level to the subject sample expression level.

In certain embodiments of the disclosed methods, amplification is performed using state-of-art polymerase chain reaction (PCR). In certain embodiments, the performance of PCR comprises an annealing time greater than 0.1, 0.5, 1, 2, 5, 8, 10 or 15 minutes. In certain embodiments, the performance of PCR comprises an extension time greater than 0.1, 0.5, 1, 2, 5, 8, 10 or 15 minutes.

In some embodiments, the disclosed methods further comprise the steps of: introducing modifications to amplified products wherein the modifications enable digestion by endonucleases; utilizing restriction endonucleases to digest the amplification products, wherein restriction endonucleases are configured to cleave DNA in the amplification product at a fixed distance away from the modifications. In some embodiments, the modification is a methylation. In some embodiments, the methylated amplified products are digested at specified restriction sites by methylation-dependent endonuclease restriction enzymes. In some embodiments, the methylation-dependent endonuclease restriction enzymes are configured to digest double-stranded DNA. In some embodiments, the methylation-dependent endonuclease restriction enzymes are configured to digest both double-stranded DNA and single-stranded DNA.

In some embodiments of the method, the target specific primers are at a concentration of 500, 250, 100, 80, 70, 50, 30, 10, 2, or 1 nM. In some embodiments, the GC content of the target-specific primers is between 40% to 70%, or 30% to 60%, or 50% to 80%. In some embodiments, the target-specific primer GC content range is less 20%, 15%, 10% or 5%. In some embodiments, the melting temperature ($T_m$) of the target-specific primers is between 55° C. to 65° C., 40° C. to 70° C., or 55° C. to 68° C. In some embodiments, the length of the target-specific primers is between 20 and 90 bases, 40 and 70 bases, 20 and 40 bases, or 25 and 50 bases. In some embodiments, the 5'-region of the modified methylated primer comprises an auxiliary sequence that is not complementary or specific for any nucleic acid region in the sample. In some embodiments, the target specific primers anneal specifically to different regions on a target region, gene or different exons of a gene. In certain embodiments, the target-specific primers are configured to anneal to target regions and simultaneously amplify the target nucleic acids in the sample.

In some embodiments, the present disclosure is directed to a method for detecting cancer in a sample. In some embodiments, the present disclosure is directed to a method for detecting the presence or absence of a congenital or inherited disease in a sample. In some embodiments, the present disclosure is directed to a method for detecting the chromosomal ploidy status in a gestating fetus in a sample, wherein the method comprises the step of measuring allele counts at polymorphic sites to determine the chromosomal ploidy state. In some embodiments, the method further comprises the step of selecting a treatment for a subject based on the target sequences detected in a sample.

In some embodiments, the target sequences comprise clinically actionable mutations. In some embodiments, the target sequences are associated with drug resistance or pharmacogenetic drug (companion diagnostic) treatment. In some embodiments, detection, identification and/or quantitation of genetic markers can be related with organ transplantation or organ rejection.

In some embodiments, the sample is obtained from a healthy subject. In some embodiments, the sample is obtained from a pregnant subject, wherein the sample comprises maternal and fetal nucleic acids. In certain embodiments, the sample is obtained from a subject that is suspected to have a disease or an elevated chance to have the disease and wherein the target sequence comprises mutations or variations that are associated with the disease. In some embodiments, the disease is cancer. In some embodiments, the sample comprises whole genomic DNA, mechanically or enzymatically fragmented DNA, cDNA, formalin-fixed paraffin-embedded tissue (FFPE), cell-free DNA (cfDNA) or circulating tumor DNA (ctDNA). In some embodiments, the sample comprises cell-free DNA from the blood plasma of a pregnant woman. In some embodiments, nucleic acid target sequences in a sample comprise single nucleotide polymorphisms (SNPs), mutations, gene rearrangements and fusions, short tandem repeats, genes, exons, coding regions and exomes. In some embodiments, the sample comprises mRNA. In some embodiments, mRNA in the sample is subjected to reverse transcription reaction to generate DNA. In some embodiments, the nucleic acids are obtained from a single cell. In some embodiments, the sample comprises nucleic acids obtained from blood, serum, plasma, spinal fluid, urine, tissue, saliva, biopsies, sputum, swabs, surgical resections, cervical swabs, tears, tumor tissue, fine needle aspiration (FNA), circulating cell-free DNA (cfDNA), and circulating tumor DNA (ctDNA), scrapings, swabs, mucus, urine, semen, hair, other non-restricting clinical or laboratory obtained samples or a forensic sample.

In one embodiment, at least one ligation adapter is a double stranded oligonucleotide comprising a sticky end and a universal priming sequence wherein the sticky end sequence of the ligation adapter is configured to be complementary to one sticky end of the digestion product produced by the methylation-dependent endonuclease restriction enzyme, wherein the universal priming sequence is used for downstream amplification and sequencing. In some embodiments, the disclosed method comprises the step of ligating at least one ligation adapter to target nucleic acids. In some embodiments, the ligation adapters comprise: (a) a universal priming sequence; (b) a barcode sequence (a DNA tagging sequence); and (c) a sticky end wherein the sticky end sequence of the ligation adapter is complementary to the sticky ends of the digestion product produced by the methylation-dependent endonuclease restriction enzyme. In some embodiments, the ligation adapter comprises: (a) a universal priming sequence; and (b) a sticky end, wherein the sticky end sequence is complementary to the digested amplicon sticky end according to the methylation-dependent endonuclease restriction enzyme used. In some embodiments, the ligation adapters comprise sticky ends complementary for both ends of the restriction enzyme digested product. In another embodiment, the ligation adapter comprises a universal priming sequence configured to allow amplification of target sequences with ligated adapter to be re-amplified. In some embodiments, the ligation step uses more than one ligation adapter.

In some embodiments, the present disclosure is directed to a method comprising the steps of: contacting target-specific primers with nucleic acids in a sample, wherein the sample comprises both maternal and fetal DNA and wherein the target-specific primers are configured to simultaneously hybridize to at least 10, 20, 100, 500, 1,000, 2,500, 5,000, 10,000, 25,000, 50,000, 80,000, 100,000 or 150,000 different target regions in nucleic acids; amplifying a plurality of target nucleic acids to produce amplicons; subjecting the amplicons to next-generation sequencing to generate sequence data; and analyzing the sequence data by a software algorithm. In some embodiments, the method further comprises the step of counting the amplicons related to the control chromosome and the suspected chromosome to determine the presence or absence of an abnormal chromosome distribution. In some embodiments, the method further comprises the step of counting the amplicons to determine presence of aneuploidy in the fetal DNA. In some embodiments, the method further comprises the step of counting the amplicons and determining the presence or absence of a deletion in the nucleic acids. In some embodiments, the sample comprises both maternal and fetal DNA. In some embodiments, the sample comprises cell-free DNA from blood plasma of a subject.

In some embodiments, the method further comprises determining the presence of aneuploidy or abnormal chromosome distribution by comparing the sample to a control sample comprising control sequences. In some embodiments, the relative quantity of the control sequences is known. In some embodiments, the relative quantity of each of the target nucleic acid sequences are standardized by a reference genome. In some embodiments, the control or reference genome includes at least one chromosomal abnormal distribution or aneuploidy. In some embodiments, the aneuploidy is at chromosome 13 or chromosome 18 or chromosome 21 or chromosome X or chromosome Y.

In some embodiments, the present disclosure is directed to a kit comprising two or more modified methylated target-specific primers configured to amplify target sequences of interest in a sample. In some embodiments, the present disclosure is directed to a kit comprising two or more modified methylated universal primers configured to amplify target sequences of interest in a sample.

BRIEF DESCRIPTION OF THE DRAWINGS

The disclosure can be better understood with reference to the following drawings. The elements of the drawings are not necessarily to scale relative to each other, emphasis instead being placed upon clearly illustrating the principles of the disclosure. Furthermore, like reference numerals designate corresponding parts throughout the several views.

FIG. 8 shows the bidirectional sequence results (electropherograms) for multiplex PCR with methylated primers (approach 1) for the oncogene EGFR with the Illumina P5 adapter sequence (SEQ ID NO: 1), sequencing primer (SEQ ID NO: 2), and Illumina P7 adapter sequence (SEQ ID NO: 3) and a reverse complement sequence with the Illumina P7 adapter sequence (SEQ ID NO: 4), sequencing primer (SEQ ID NO: 5), and Illumina P5 adapter sequence (SEQ ID NO: 6).

DETAILED DESCRIPTION

Figure 1:
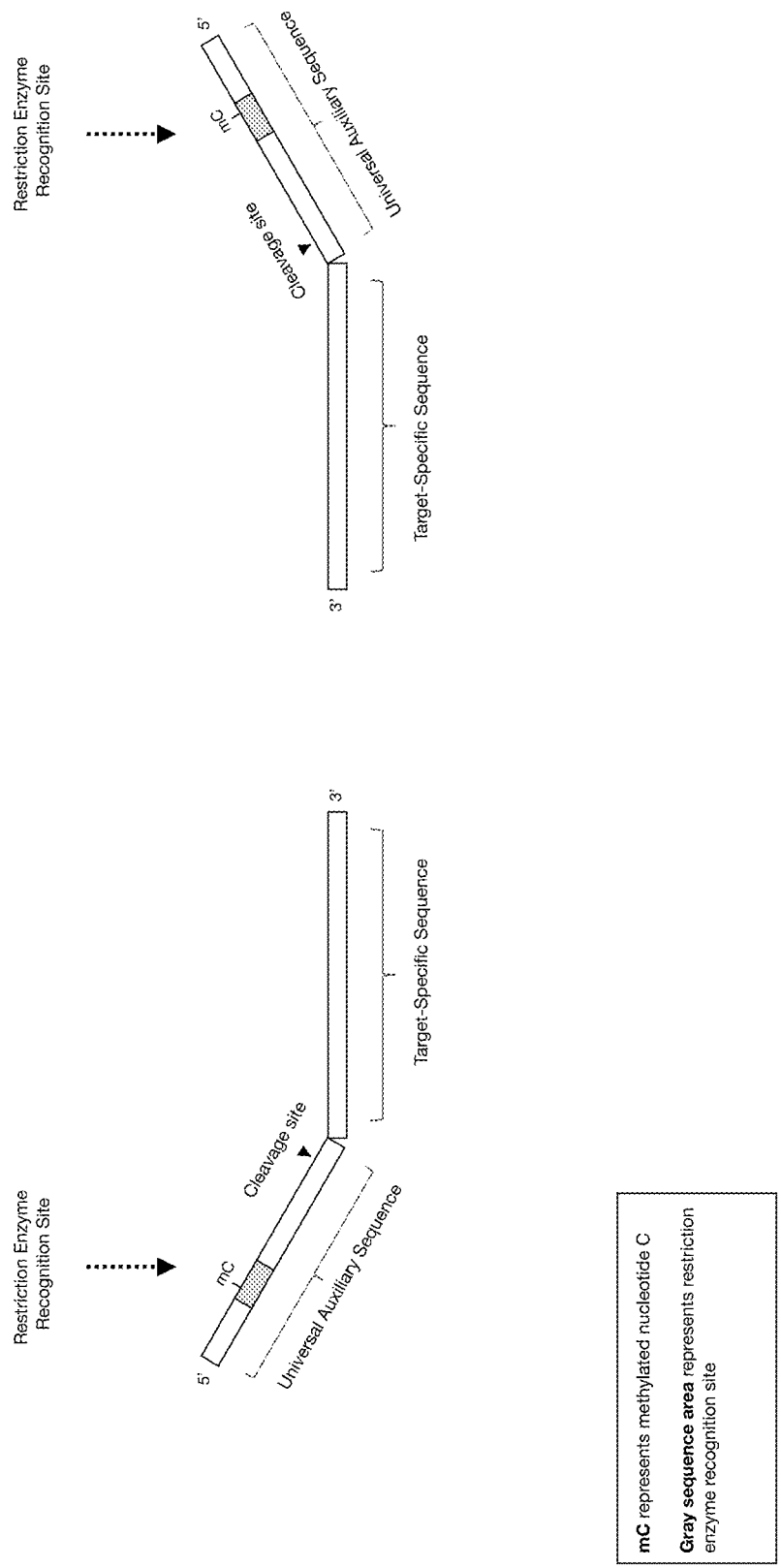
FIG. 1 illustrates a schematic image of forward and reverse methylated target-specific primers. Each primer consists of a target-specific sequence portion, and a universal auxiliary sequence portion consisting of a methylated nucleotide C (mC), a restriction enzyme recognition site and a cleavage site.

The present disclosure relates to methods and compositions for the amplification and enrichment of specific target sequences. The following examples, applications, descriptions and content are exemplary and explanatory, and are non-limiting and non-restrictive in any way. The present disclosure features a variety of applications, such as genotyping, detection of chromosomal abnormalities (such as a fetal chromosome aneuploidy), gene mutation and polymorphism (such as single nucleotide polymorphisms, SNPs) analysis, gene deletion, determination of paternity, analysis of genetic differences among populations, forensic analysis, measuring predisposition to disease, quantitative analysis of mRNA, and detection and identification of infectious agents (such as bacteria, parasite, and viruses). The methods disclosed herein can also be used for non-invasive prenatal testing, such as paternity testing or the detection of fetal chromosome abnormalities.

Next-generation sequencing has enabled many applications at an extremely low cost, but certain applications such as whole genome sequencing and whole transcriptome sequencing, although practical for research settings and discovery, remain impractical in clinical settings for the diagnosis, treatment and prognosis of disease. Specific and uniform multiplex target sequencing presents many advantages in both clinical and research settings. To increase the output and efficacy of biological assays, such as multiplex PCR and next-generation sequencing, simultaneous amplification of many target genes using a combination of several target specific primers allows multiplex amplification of regions of interest. Although the use of many primers reduces labor, cost and time, the resulting non-specific amplifications or amplification artifacts such as primer-primer interactions (primer-dimers) and superamplicons can interfere with optimal amplification and further analysis, such as sequencing. These artifacts waste PCR reaction reagents and generate shorter fragments in lieu of the intended target sequences. Further, these unwanted non-specific fragments tend to dominate the amplification reaction, because they are amplified more efficiently than the desired target sequences. These undesired artifacts may also interfere with downstream procedures and applications that involve a second PCR step, such as next-generation sequencing. These artifacts may consume a sizeable portion of sequence reads, generating non-informative results.

A current problem with target enrichment—whereby genomic regions from a DNA sample are selectively captured before sequencing—is achieving high specificity and uniformity, which would require fewer sequencing reads to generate adequate coverage and sequence data for downstream analysis. In certain applications, such as cancer or genetic diseases, much deeper sequencing is needed to detect, identify or verify somatic mutations with high specificity and uniformity in the panel.

Further, the need remains to minimize primer-dimers, which would allow for the development of highly multiplex PCR whereby multiplex amplification could simultaneously amplify a large number of target nucleic acids in a single test reaction. Moreover, removal of primer-dimers would allow an increased number of primers for multiplexing, higher concentrations of primers for balanced amplification and higher sensitivity. The ability to increase the number of target-specific in a multiplex PCR would allow for the simultaneous amplification of a large number (thousands) of nucleic acid targets while also decreasing the amount of input DNA, labor and time. This would be especially advantageous when the amount of starting input nucleic acid material is limited, or the sample is nucleic acid from a single cell.

To address the foregoing needs, herein described is a method of multiplex target enrichment using methylated primers to remove primer-dimers to increase and expand the multiplex primer capability for further analysis such as next-generation sequencing. The method can be used in two approaches. In the first approach, the target-specific primers contain a methylated C (mC) in the universal auxiliary portion, and in the second approach the two universal auxiliary primers contain methylated C (mC) and are used in combination with target-specific primers containing a portion complementary to methylated universal auxiliary primer.

Thus, the present disclosure can be performed in two variant approaches. The first approach is a method comprising the steps of: (1) contacting methylated target-specific primers with nucleic acid target sequences in a sample to hybridize the methylated target-specific primers to the target sequences in the sample; (2) subjecting the target nucleic acid sequences to amplification under optimal amplification conditions to form an amplified product; (3) subjecting the amplified product to digestion with a methylation-dependent endonuclease restriction enzyme to form a digestion product, wherein the digested product contains sticky ends on each end of the strands; (4) performing size selection purification on the digestion product for removal of digested primer-dimers and unused primers to form a selected digestion product; (5) ligating universal adapters to dsDNA in the selected digestion product to form a ligated product, wherein the universal adapters comprise complementary sticky ends to ds DNA and a universal sequence portion; (6) subjecting the ligated product to amplification using barcoded universal primers to form a final amplification product, wherein the barcoded universal primers are configured to be complementary to a sequence on the ligation adapters; and (7) preparing the final amplification product for next-generation sequencing.

The second approach is method comprising the steps of: (1) contacting target-specific primers with nucleic acid target sequences in a sample to hybridize the target-specific primers to the target sequences, wherein the target-specific primers comprise a universal auxiliary portion at the 5'-end; (2) subjecting the target sequences to a first amplification with universal auxiliary primers under optimal amplification conditions to form an amplified product; (3) subjecting a portion of the amplified product to a second amplification using methylated universal auxiliary primers to form a second amplified product, wherein the methylated universal auxiliary primers comprise a restriction enzyme recognition sequence; (4) subjecting the second amplified product to digestion with a methylation-dependent endonuclease restriction enzyme to form a digested product, wherein the digested product contains sticky ends on each end of the strands; (5) performing size selection purification on the digested product to remove digested primer-dimers and unused primers to form a selected digested product; (6) ligating universal adapters to ds DNA in the selected digested product to form a ligated product, wherein the universal adapters comprise complementary sticky ends and a universal sequence portion; (6) subjecting the ligated product to a third amplification using barcoded universal primers to form a final amplification product, wherein the barcoded universal primers comprise a sequence complementary to sequences on the ligation adapters; and (7) quantifying the final amplification product for next-generation sequencing.

The disclosed methods may further comprise the step of extracting DNA from a sample, such as FFPE or blood, plasma DNA or RNA (converted to ds cDNA). The disclosed methods may further comprise purification known to those of skill in the art. The disclosed methods may comprise about 10, 20, 100, 500, 1,000, 2,500, 5,000, 10,000, 25,000, 50,000, 80,000, 100,000 or 150,000 or greater target-specific primers and about 10, 20, 100, 500, 1,000, 2,500, 5,000, 10,000, 25,000, 50,000, 80,000, 100,000 or 150,000 or greater target sequences.

A subject may be a mammal. In some instances, the subject is a human. The subject may be healthy, diagnosed with a disease, or suspected of having a disease. In other instances, the subject may be non-mammalian, such as a bacterium, virus, or fungus.

Target nucleic acids may be present in a sample obtained from a subject. A sample can comprise proteins, cells, fluids, biological fluids, preservatives, blood, hair, biopsy materials, and other material that contains nucleic acids. The nucleic acid sample may comprise genomic DNA or RNA. The sample may also comprise nucleic acid molecules obtained from FFPE or archived DNA samples. The sample may also comprise mechanically or enzymatically sheared or fragmented DNA. The sample may comprise circulating cell-free DNA (cfDNA) such as material obtained from a maternal subject, or circulating tumor DNA (ctDNA) from a subject diagnosed with cancer or from a subject for cancer screening purposes. The sample may comprise nucleic acid molecules obtained from blood, serum, plasma, spinal fluid, urine, tissue, saliva, biopsies, sputum, swabs, formalin-fixed paraffin-embedded material (FFPE), surgical resections, cervical swabs, tears, tumor tissue, fine needle aspiration (FNA), circulating cell-free DNA (cfDNA), and circulating tumor DNA (ctDNA), scrapings, swabs, mucus, urine, semen, hair, laser capture microdissections, and other non-restricting clinical or laboratory obtained samples. The sample may be an epidemiological, bacterial, viral, fungi, agricultural, forensic or pathogenic sample.

Figure 2:
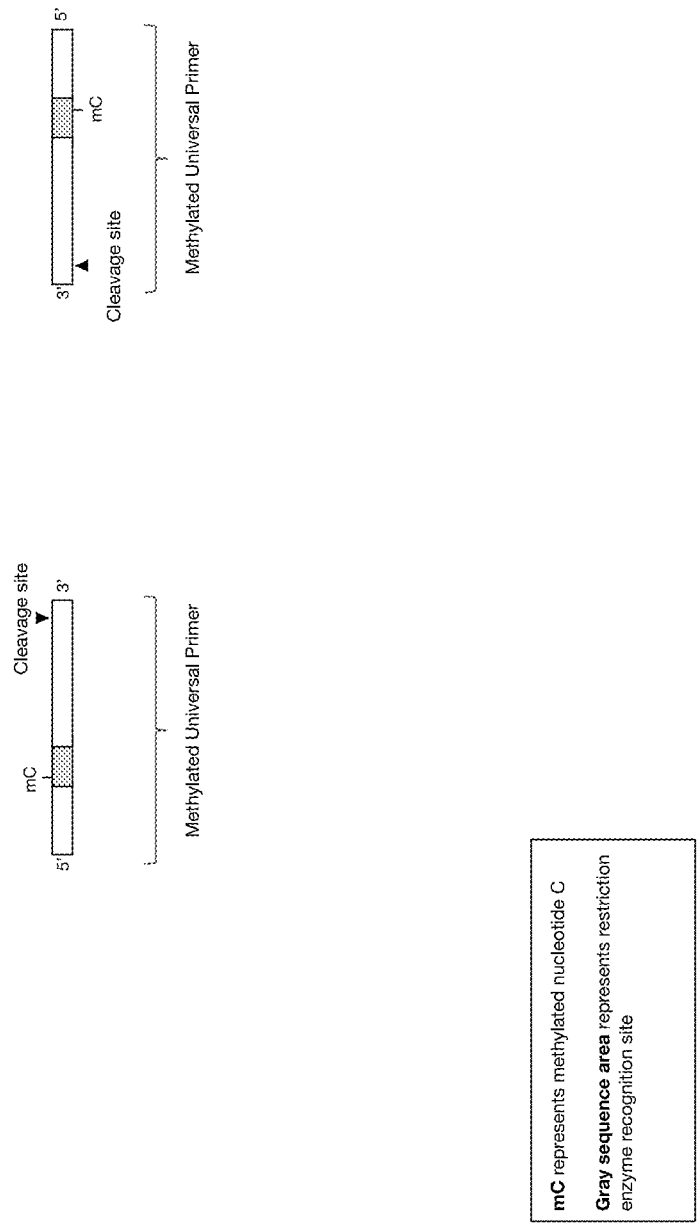
FIG. 2 illustrates a schematic diagram of forward and reverse universal auxiliary methylated primer for the second approach. The universal auxiliary sequence primer consists of a methylated nucleotide C (mC), a restriction enzyme recognition site and a cleavage site.
Figure 3:
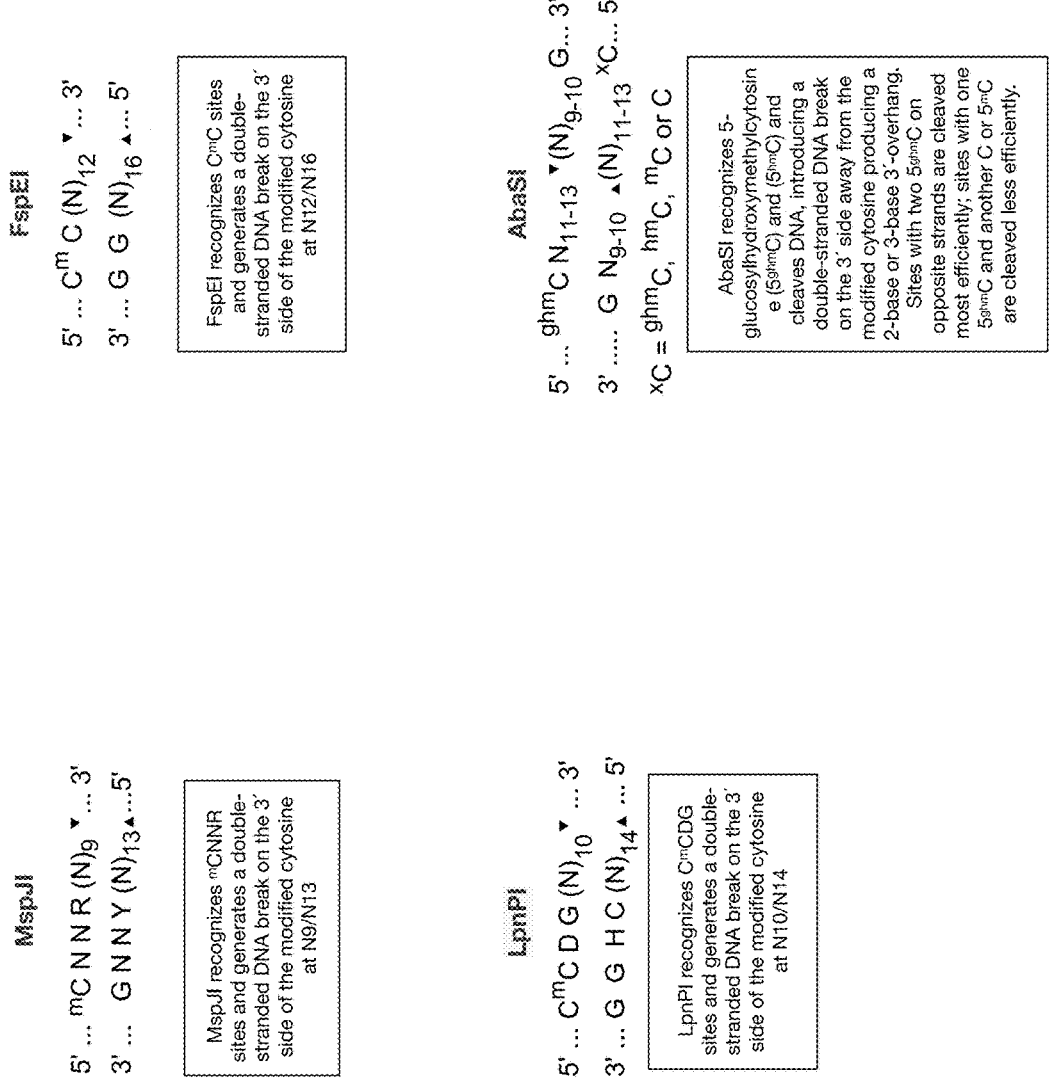
FIG. 3 shows four examples of modification-dependent endonucleases and their restriction sites. The methylation-dependent endonuclease restriction enzymes digest the modified (methylated) cytosine in the double-stranded DNA at the shown restriction site.
Figure 4:
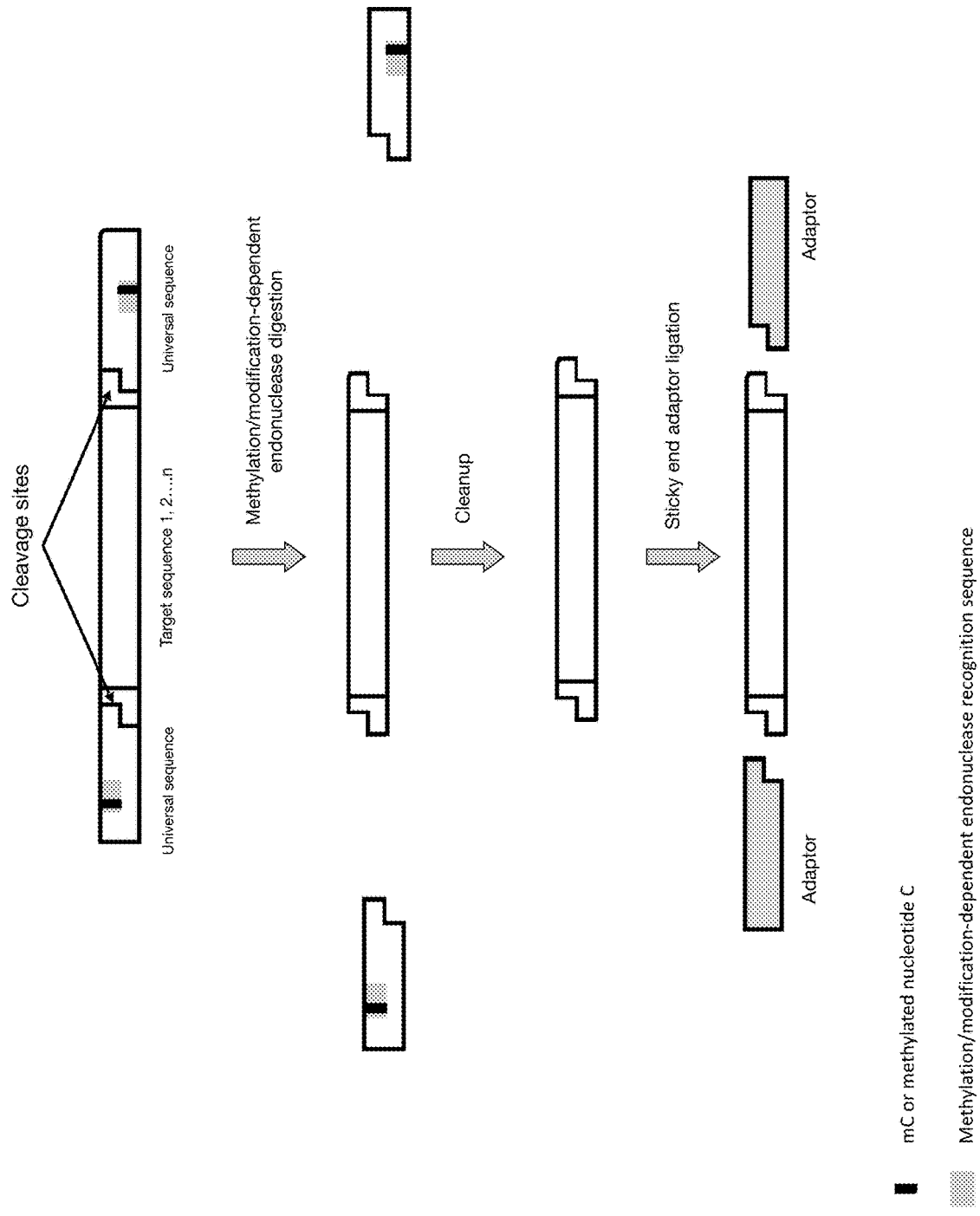
FIG. 4 illustrates an amplicon amplified with methylated primers (approach 1 or 2) and digestion by methylation/modification-dependent endonuclease enzyme. The digested primers and excess/unused primers are removed by size selection cleanup and complementary sticky-end adaptors are ligated to sticky-end amplicons.
Figure 5:
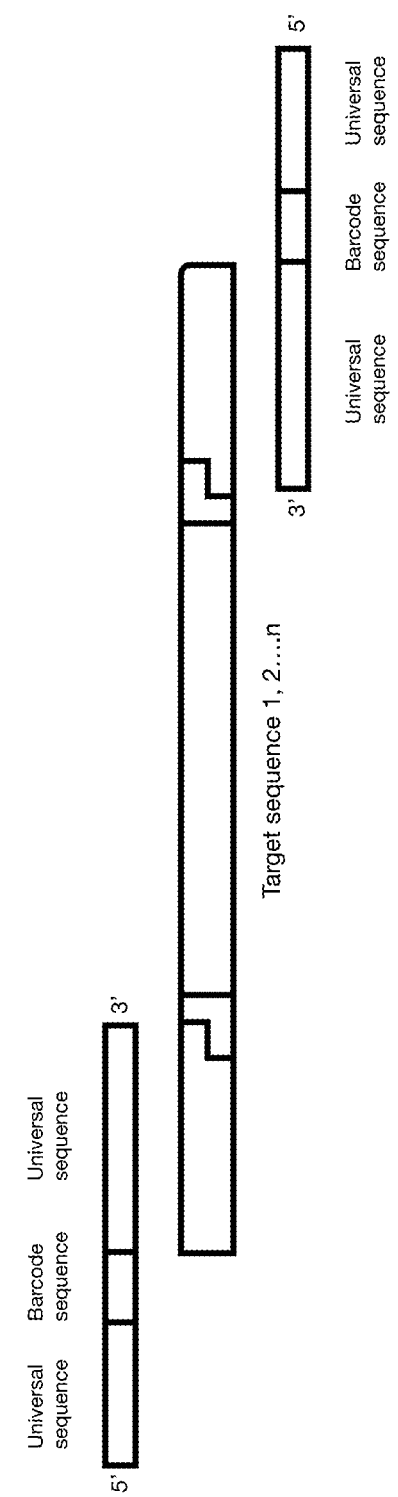
FIG. 5 shows amplification of adaptor-ligated amplicons with barcoded universal primers prior to library preparation and sequencing.
Figure 6:
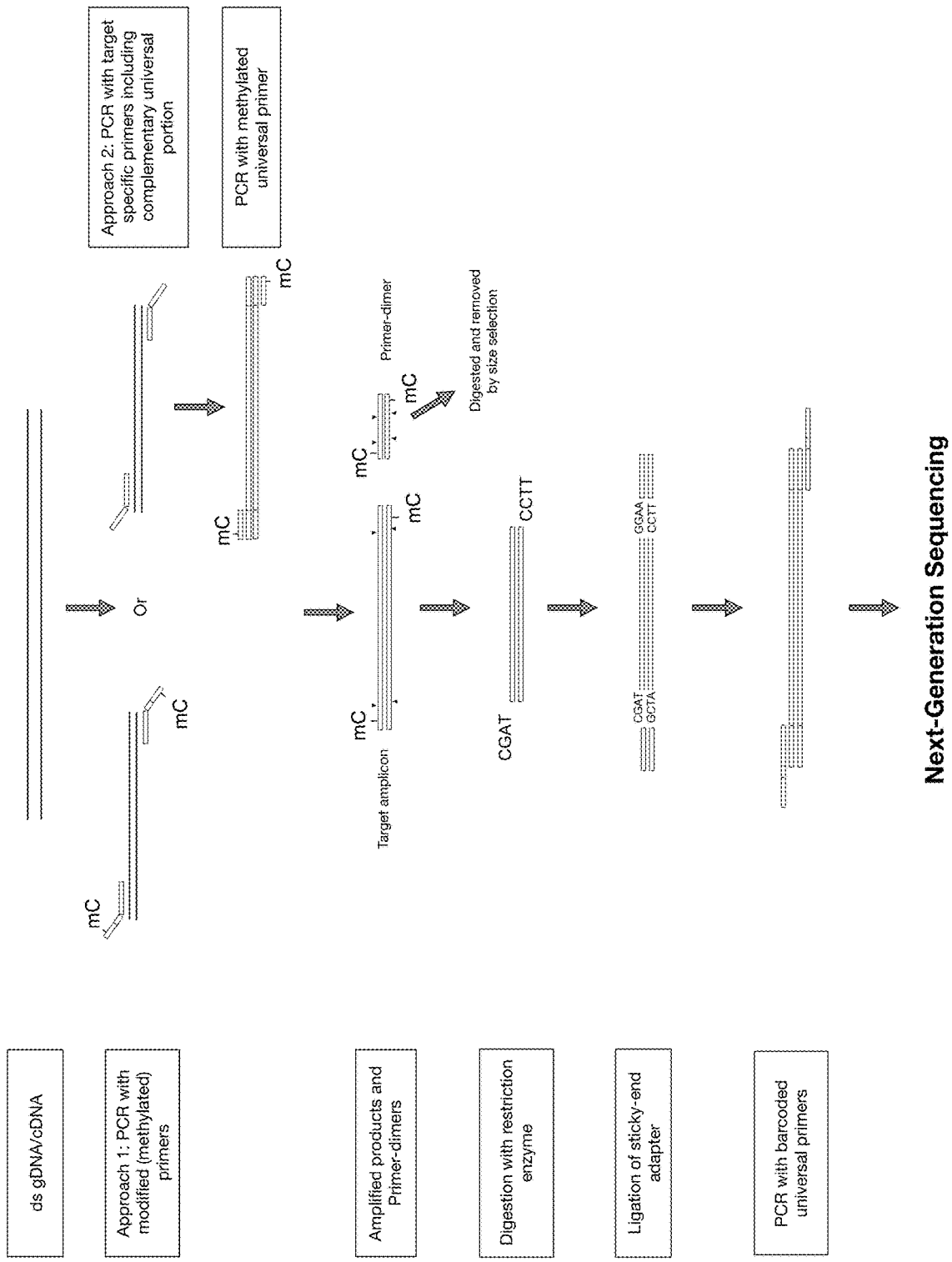
FIG. 6 depicts a schematic drawing of the overall library preparation wherein: (1) double stranded gDNA or RNA (converted to cDNA) are amplified by either methylated target-specific primers, wherein the methylation is on the auxiliary sequence portion (approach 1); or amplification using target-specific primers that comprise a universal auxiliary sequence to form an amplified product, and then using a portion of the amplified product for the next PCR using methylated universal auxiliary primer (approach 2); (2) digesting either amplified product from (1) with methylation-dependent endonuclease restriction enzyme, wherein the amplified product contains sticky ends on each end of the strands, and performing size selection purification for removal of digested primer-dimers and unused primers; (3) ligating universal adapters comprising complementary sticky ends to dsDNA wherein the ligation adapter comprises a universal sequence portion; (4) subjecting the ligated product to amplification with barcoded universal primers complementary to sequences on the ligation adapters to form a final amplification product; and (5) preparing the final amplification product for next-generation sequencing.
Figure 7:
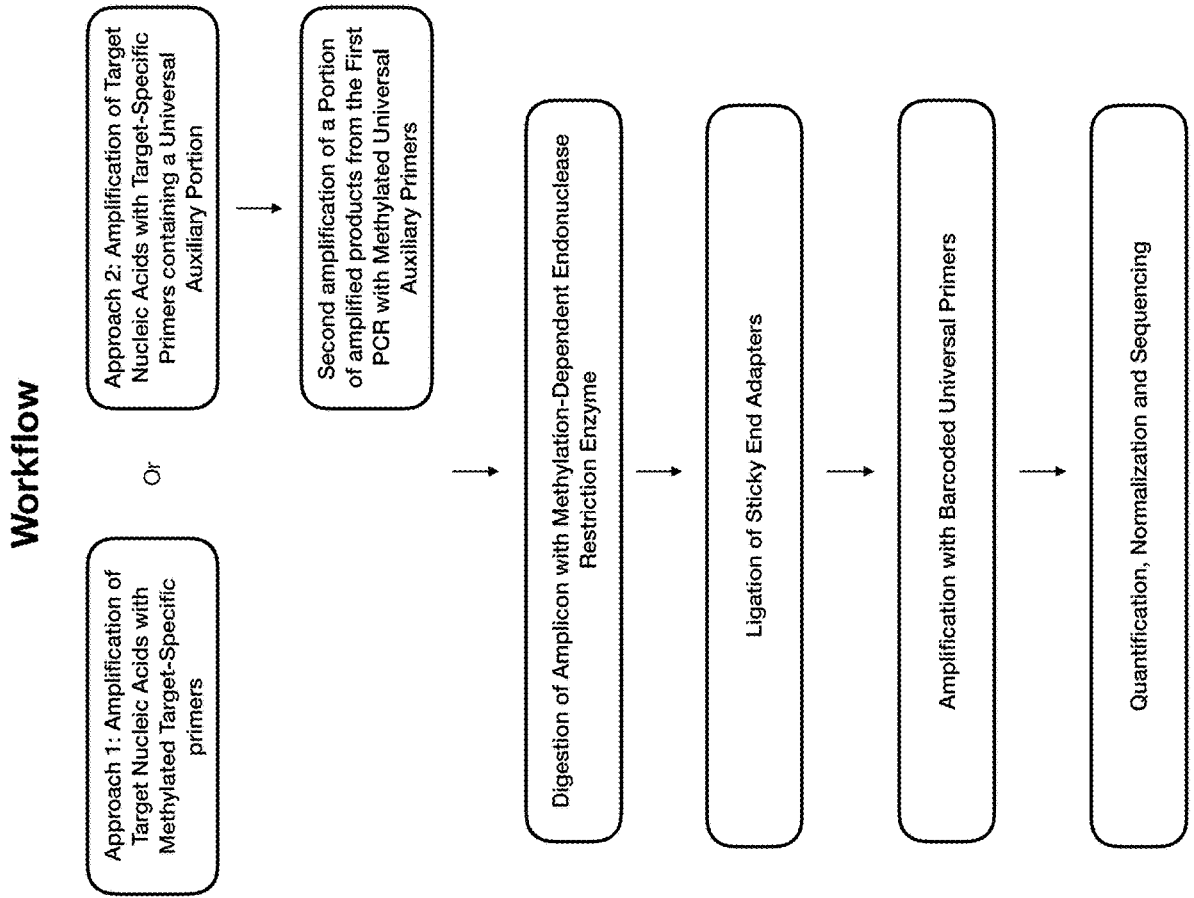
FIG. 7 illustrates library preparation workflow for the two methods disclosed by FIG. 6.
Figure 9:
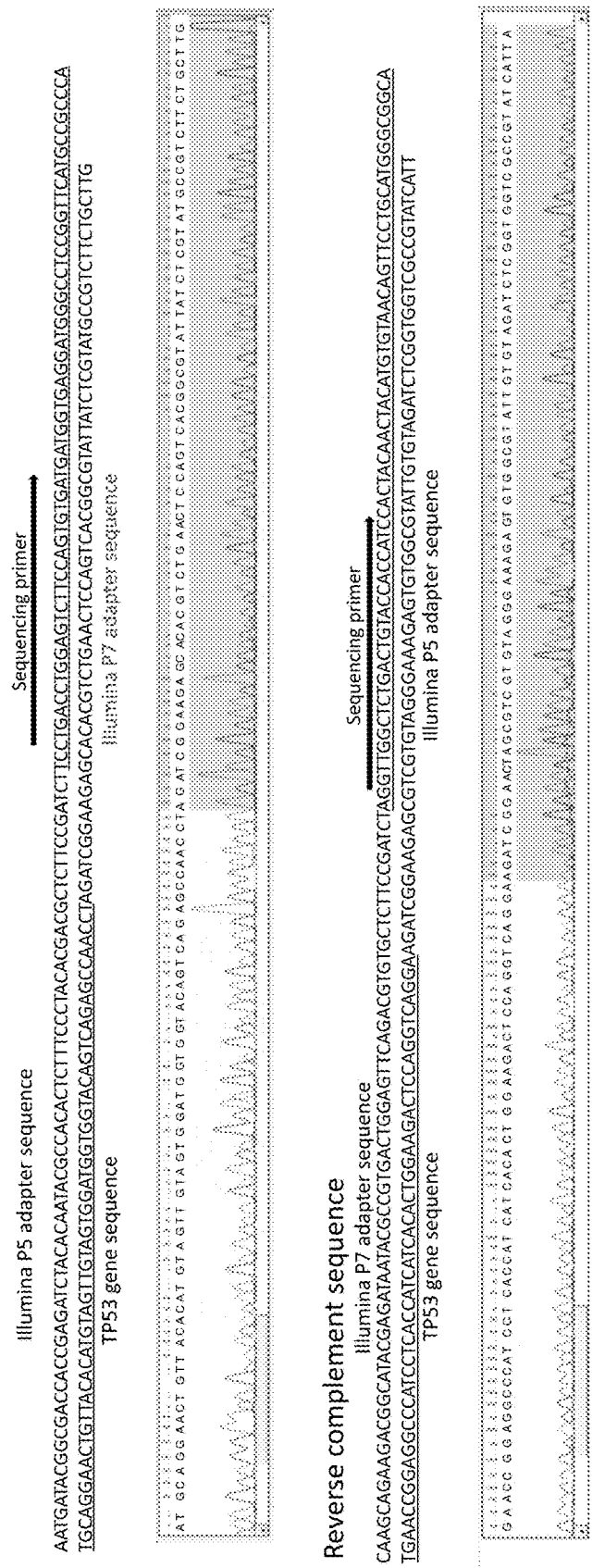
FIG. 9 shows the bidirectional sequence results (electropherograms) for multiplex PCR with methylated primers (approach 1) for the oncogene TP53 with the Illumina P5 adapter sequence (SEQ ID NO: 1), sequencing primer (SEQ ID NO: 7), and Illumina P7 adapter sequence (SEQ ID NO: 3) and a reverse complement sequence with the Illumina P7 adapter sequence (SEQ ID NO: 4), sequencing primer (SEQ ID NO: 8), and Illumina P5 adapter sequence (SEQ ID NO: 6).
Figure 10:
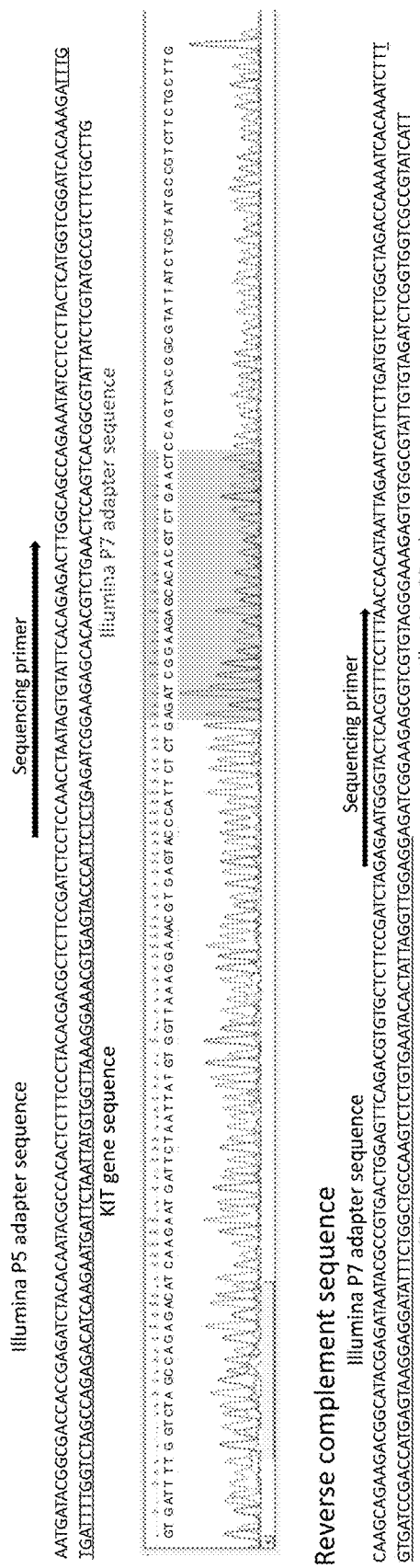
FIG. 10 shows the bidirectional sequence results (electropherograms) for multiplex PCR with methylated primers (approach 1) for the oncogene KIT with the Illumina P5 adapter sequence (SEQ ID NO: 1), sequencing primer (SEQ ID NO: 9), and Illumina P7 adapter sequence (SEQ ID NO: 3) and a reverse complement sequence with the Illumina P7 adapter sequence (SEQ ID NO: 4), sequencing primer (SEQ ID NO: 10), and Illumina P5 adapter sequence (SEQ ID NO: 6).
Figure 11A:
FIGS. 11A and 11B show screenshots of Illumina sequence reads from library generated with approach 2 disclosed in this invention, mapped onto human sequence reference hg19 for different targeted regions for KRAS (FIG. 11A) and KIT (FIG. 11B).
Figure 11B:
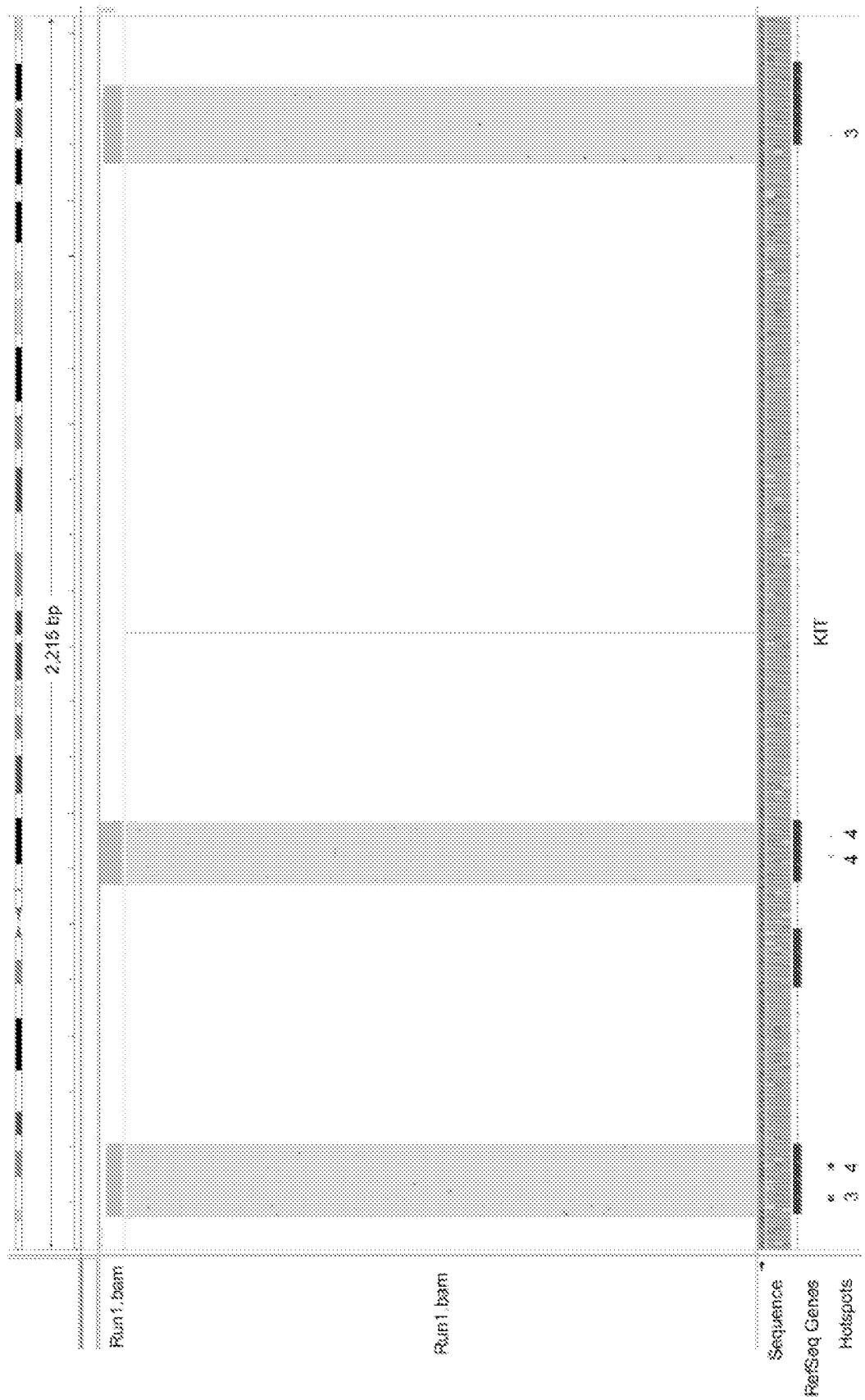

A plurality of target-specific primers may comprise a target-specific sequence and an auxiliary sequence at the 5'-, wherein the auxiliary sequence is configured to allow digestion of a methylated site using a restriction enzyme. Further, the methylation can either be directly situated on the auxiliary portion of a target-specific primer on the universal auxiliary primer. The target-specific primers may comprise a methylated universal auxiliary sequence portion that comprises a restriction enzyme recognition site and a target-specific sequence portion (FIG. 1). Amplification may utilize at least one forward target-specific primer and at least one reverse target-specific primer. The target-specific primers may comprise a universal auxiliary sequence. The present disclosure also contemplates a method wherein target-specific primers, comprising a universal auxiliary portion, are used in the first amplification, and wherein complementary methylated universal auxiliary primers, comprising a methylated nucleotide and a restriction enzyme recognition site, are used for the second amplification (FIG. 2). The target-specific primers may be configured to hybridize to short tandem repeats (STRs) of target sequences. The target-specific primers can include a nucleotide modification in the 3'-end, the 5'-end, or across the sequence. The length of target-specific portion of the target-specific primer can be about 15 to 40 bases. The $T_m$ of each target-specific primer can be about 50° C. to about 72° C. or other ranges of temperature.

The target-specific primers may be directed to at least one target sequence whereby one or more mutations in target sequence are indicative of a subject having a disease. The mutation may be a clinically actionable mutation. The mutation may also be associated with drug resistance or a companion diagnostic treatment. Mutations can include substitutions, insertions, inversions, point mutations, deletions, mismatches and translocations. In one embodiment, the mutations can include variation in copy number. In one embodiment, the mutations can include germline or somatic mutations. In some embodiments, the mutations have less than about a 10% allele frequency. In other embodiments, the mutations have less than about a 5%, 3%, 1%, 0.5%, 0.1% or 0.01% allele frequency.

The target-specific primers may target a sequence associated with disease related to cancer or one or more autoimmune, genetic, cardiovascular, developmental, metabolic, neurological, neuromuscular disorders, newborn diseases or newborn disorders. The target sequence may be associated with organ transplantation or organ rejection.

The target-specific primers may be directed to one or more genes associated with high-prevalence clinically relevant cancer genes covering many cancers. The target-specific primers may be configured to amplify one or more clinically relevant genes for cancer including, but not limited to: AIP, ALK, APC, ATM, BAP1, BARD1, BLM, BMPR1A, BRCA1, BRCA2, BRIP1, CDH1, CDK4, CDKN1B, CDKN2A, CHEK2, DICER1, EPCAM, FANCC, FH, FLCN, GALNT12, GREM1, HOXB13, MAX, MEN1, MET, MITF, MLH1, MRE11A, MSH2, MSH6, MUTYH, NBN, NF1, NF2, PALB2, PHOX2B, PMS2, POLD1, POLE, POT1, PRKAR1A, PTCH1, PTEN, RAD50, RAD51C, RAD51D, RB1, RET, SDHA, SDHAF2, SDHB, SDHC, SDHD, SMAD4, SMARCA4, SMARCB1, SMARCE1, STK11, SUFU, TMEM127, TP53, TSC1, TSC2, VHL, and XRCC2.

The target-specific primers may also be directed to one or more genes associated with breast cancer. The target-specific primers may be configured to amplify one or more clinically relevant genes for breast cancer including, but not limited to: ATM, BARD1, BRCA1, BRCA2, BRIP1, CDH1, CHEK2, FANCC, MRE11A, MUTYH, NBN, NF1, PALB2, PTEN, RAD50, RAD51C, RAD51D, STK11, and TP53.

The target-specific primers may be directed to one or more genes associated with ovarian cancer. The target-specific primers may be configured to amplify one or more clinically relevant genes for ovarian cancer including, but not limited to: ATM, BARD1, BRCA1, BRCA2, BRIP1, CDH1, CHEK2, DICER1, EPCAM, MLH1, MRE11A, MSH2, MSH6, MUTYH, NBN, NF1, PALB2, PMS2, PTEN, RAD50, RAD51C, RAD51D, SMARCA4, STK11, and TP53.

The target-specific primers may be directed to one or more genes associated with colorectal cancer. The target-specific primers may be configured to amplify one or more clinically relevant genes for colorectal cancer including, but not limited to: APC, BMPR1A, CDH1, CHEK2, EPCAM, GREM1, MLH1, MSH2, MSH6, MUTYH, PMS2, POLD1, POLE, PTEN, SMAD4, STK11, and TP53.

The target-specific primers may be directed to one or more genes associated with prostate cancer. The target-specific primers may be configured to amplify one or more clinically relevant genes for prostate cancer including, but not limited to: ATM, BRCA1, BRCA2, CHEK2, EPCAM, HOXB13, MLH1, MSH2, MSH6, NBN, PALB2, PMS2, RAD51D, and TP53.

The target-specific primers may be directed to detection and identification of fusion genes such as abnormal gene fusions or transforming gene fusions (example EML4-ALK or ROS1) in cancer. The target-specific primers may be configured to amplify one or more fusion genes in cancer including, but not limited to: AKT3, ALK, ARHGAP26, AXL, BRAF, BRD3, BRD4, EGFR, ERG, ESR1, ETV1, ETV4, ETV5, ETV6, EWSR1, FGFR1, FGFR2, FGFR3, FGR, INSR, MAML2, MAST1, MAST2, MET, MSMB, MUSK, MYB, NOTCH1, NOTCH2, NRG1, NTRK1, NTRK2, NTRK3, NUMBL, NUTM1, PDGFRA, PDGFRB, PIK3CA, PKN1, PPARG, PRKCA, PRKCB, RAF1, RELA, RET, ROS1, RSPO2, RSPO3, TERT, TFE3, TFEB, THADA, and TMPRSS2.

The target-specific primers may be configured to amplify selectively target sequences carrying mutations that are associated with a congenital or inherited disease. The mutations can be somatic or germline mutations. Mutations associated with a congenital or inherited disease can include point mutations, insertions, deletions, inversions, substitutions, mismatches, translocations and copy number variations. In some embodiments, at least one of the target-specific primers associated with an inherited disease is at least 90% complementary to the target sequence.

The target-specific primers may be directed to one or more genes associated with cardiovascular disease. The target-specific primers may be configured to amplify one or more clinically relevant genes associated with cardiovascular disease including, but not limited to: ABCC9, ACTA2, ACTC1, ACTN2, AKAP9, ANK2, ANKRD1, BAG3, CACNA1C, CACNA2D1, CACNB2, CALM1, CASQ2, CAV3, CBS, COL3A1, COL5A1, COL5A2, CRYAB, CSRP3, DES, DMD, DSC2, DSG2, DSP, EMD, EYA4, FBN1, FBN2, FKTN, FLNA, FXN, GATA4, GATAD1, GLA, GPD1L, HCN4, JAG1, JPH2, JUP, KCND3, KCNE1, KCNE2, KCNE3, KCNH2, KCNJ2, KCNJ5, KCNJ8, KCNQ1, LAMA4, LAMP2, LDB3, LMNA, MED12, MYBPC3, MYH11, MYH6, MYH7, MYL2, MYL3, MYLK, MYOZ2, MYPN, NEXN, NKX2-5, NOTCH1, PKP2, PLN, PLOD1, PRKAG2, PRKG1, PTPN11, RAF1, RBM20, RYR2, SCN1B, SCN2B, SCN3B, SCN4B, SCN5A, SKI, SLC2A10, SMAD3, SMAD4, SNTA1, TAZ, TBX1, TBX20, TBX5, TCAP, TGFB2, TGFB3, TGFBR1, TGFBR2, TMEM43, TMPO, TNNC1, TNNI3, TNNT2, TPM1, TRDN, TRPM4, TTN, TTR, TXNRD2, and VCL.

The present disclosure also relates to a method of target enrichment by multiplex PCR, comprising the steps of contacting target sequences with a plurality of target-specific primers in the presence of PCR reagents such as DNA polymerase, dNTPs and reaction buffer; and given the optimal conditions of temperature and time for denaturation, annealing and extension, hybridizing the primers complementary target sequences and extending such target sequences. Amplification, purification and cleanup may be adjusted or removed as needed for optimization of multiplex target amplification for downstream processes as determined by one of skill in the art.

The methods disclosed herein feature a broad range of applications in clinical and research settings and can be used for mutation detection and analysis, single nucleotide polymorphisms (SNPs), microbial and viral detection, deletions and insertions, genotyping, copy number variations (CNV), epigenetic and methylation analysis, gene expression, transcriptome analysis, and low frequency allele mutations. The disclosed methods can also be used for the detection, diagnostics, prognosis and treatment of disease. The disclosed methods can also detect both germline or somatic mutations in a sample.

The disclosed methods may use PCR and DNA polymerase. A wide selection of DNA polymerases are available, which feature different characteristics such as thermostability, high-fidelity, processivity and Hot Start. Amplification conditions, such as number of cycles, annealing temperature, annealing duration, extension temperature and extension duration, may be adjusted to optimal conditions for amplification, which may be based on the instructions provided with the commercial DNA polymerase that is selected. The concentration of DNA polymerase for multiplex PCR can be higher than for single-plex PCR.

The ligation adapters used by the methods disclosed herein are double-stranded and are configured to ligate to double-stranded nucleic acid fragments. The ligation adapters comprise a universal sequence portion that is non-complementary to target sequences and a sticky end complementary to the sticky-end on digested amplicons. The barcode sequence on the barcoded universal primer allows tagging nucleic acid fragments of each subject and can discriminate the identity of each sample. As such, barcoding increases throughput by enabling the pooling of samples. The disclosed methods may also use the ligation adapters for the purpose of universal amplification of a large number of nucleic acid target sequences.

The disclosed methods amplify target sequences using multiplex polymerase chain reaction, wherein more than one target sequence is amplified in a single test reaction. The amount of nucleic acid in a sample needed for multiplex amplification can be about 1 ng. Alternatively, the amount of nucleic acid material can be about 5 ng, 10 ng, 50 ng, 100 ng or 200 ng or more. Multiplex polymerase chain reaction can be performed on a thermocycler and each cycle of the multiplex PCR comprises the steps of denaturation, annealing and extension. Each cycle of the multiplex PCR includes at least one denaturation step, one annealing step and one extension step for extension of nucleic acids. The disclosed methods can comprise 5 to 20 cycles of PCR in each round of amplification, although other numbers of cycles are possible. For example, between 1 and 10 cycles, between 1 and 15 cycles, between 1 and 20 cycles, between 1 and 25 cycles, or between 1 and 30 cycles or more can be performed. Each cycle or set of cycles can have different durations and temperatures. For example, the annealing step can have incremental increases and decreases in temperature and duration or the extension step can have incremental increases and decreases in temperature and duration. The duration can have decreases or increases of about 5 seconds, 10 seconds, 30 seconds, 1 minute, 2 minutes, 4 minutes, 8 minutes or greater increments. The temperature can have decreases or increases in about 0.5, 1, 2, 4, 8, 10 Celsius or greater increments.

Amplicon size selection can be used to sequence amplified products of a certain length range. For example, amplicons of 100 to 250 base pairs, 150 to 300 base pairs, 120 to 350 base pairs, or 200 to 500 base pairs or greater length range can be sequenced.

Typically, a small number of primers in a primer set or primer pool cause amplification artifacts such as primer-dimers in multiplex amplification reactions. By employing a primer selection algorithm that can calculate the undesired primer-primer interactions, however, target-specific primer selection can be performed in an efficient manner that minimizes primer-primer interactions to negligible amount, allowing multiplex amplification capable of simultaneously amplifying a large number of target sequences in a single test reaction. Moreover, the digestion of a methylation site on the universal portion of target-specific primers allows the removal of primer-dimers by methylation-dependent endonuclease restriction enzyme digestion and size selection purification such as SPRIselect beads. Furthermore, methylated target-specific primers allow increased number of primers for multiplexing, higher concentrations of target-specific primers for balanced amplification and higher sensitivity without concerns for primer-dimers. The ability to increase the number of target-specific primers in a multiplex PCR allows the simultaneous amplification of a large number (thousands) of nucleic acid target sequences while decreasing the amount of input DNA, labor and time. This is especially advantageous when the amount of starting input nucleic acid material is limited, or when the sample comprises nucleic acid from a single cell.

Primer dimers can be reduced or minimized by adjusting different parameters of the disclosed methods, such as the duration of annealing steps, temperature increments, and/or the number of cycles of PCR. The primer concentrations can be lowered, and annealing temperature and duration can be increased to allow specific amplification (the primers have more time interval to hybridize to target nucleic acids) in addition to reduced or minimal primer dimers. The concentration of target-specific primers can be about 500 nM, 250 nM, 100 nM, 80 nM, 70 nM, 50 nM, 30 nM, 10 nM, 2 nM, 1 nM or lower than 1 nM. Alternatively, the concentration of each target-specific primer can be between 1 µM to 1 nM, between 1 nM to 80 nM, between 1 nM to 100 nM, between 10 nM to 50 nM, or between 1 nM to 60 nM. The annealing temperature can be about 1 minute, 3 minutes, 5 minutes, 8 minutes, 10 minutes or longer. Amplification with increased annealing times may use 1 cycle, 2 cycles, 3 cycles, 5 cycles, 8 cycles, 10 cycles or more cycles followed by standard annealing durations.

The disclosed methods and kits may comprise at least 10, 20, 100, 500, 1,000, 2,500, 5,000, 10,000, 25,000, 50,000, 80,000, 100,000 or 150,000 or more target-specific primers, wherein each target-specific primer is directed to hybridize to a specific target sequence. There can be more than one set of target-specific primers; as an example, there can be two sets of target-specific primers for two test reactions, 3 sets for 3 test reactions or 5 sets for 5 test reactions or more. For practical reasons, such as limitations in target-specific primer design or selection, the sample may also be split into multiple parallel multiplex test reactions with multiple sets of target-specific primers.

The GC content of target-specific primers can be between 40% to 70%, between 30% to 60%, between 50% to 80%, or between 30 to 80%. Alternatively, the target-specific primer GC content range can be less 20%, 15%, 10% or 5%. The melting temperature ($T_m$) of the target-specific primers can be between 55° C. to 65° C., between 40° C. to 70° C., between 50° C. to 68° C., or such other range as determined by one of skill in the art. The melting temperature range of the target-specific primers can vary. In some instances, the range can be less 20° C., 15° C., 10° C., 5° C., 2° C. or 1° C. The length of the target-specific primers can also vary. In some instances, the length can be between 20 to 90 bases, 40 to 70 bases, 20 to 40 bases or 25 to 50 bases. The range of length of the target-specific primers can also vary. For instance, it can be 60, 50, 40, 30, or 20 bases. In some instances, the 5'-region of the target-specific primer is an auxiliary or universal primer binding site or a tag and is not complementary or specific for any target sequence. In some instances, the length of the target sequence is between 50 and 500 bases, 90 to 350 bases, or 200 to 450 bases, although other lengths are possible.

The present disclosure is also directed to a kit that comprises two or more target-specific primers. In some instances, the kit comprises a plurality of methylated target-specific primers. In other instances, the kit comprises a combination of methylated universal primers and target-specific primers. The target-specific primers are designed and selected based on criteria described to have no or minimal primer-primer interactions or non-specific priming. The kit can be formulated for detection, diagnosis, prognosis and treatment of disease such as cancer or congenital or inherited disease. The kit can also be configured for ploidy status of a gestating fetus, for example by selecting target-specific primers that target sequences on chromosomes that are associated with trisomy in fetus such as chromosomes 13, 18, 21, X and Y, other chromosome, or some combination thereof. The kit may comprise about 10, 20, 100, 500, 1,000, 2,500, 5,000, 10,000, 25,000, 50,000, 80,000, 100,000 or 150,000 or greater target-specific primers.

The methods and kits disclosed herein may comprise a plurality of target-specific primers having no or minimal self-complementary structure and that do not form a secondary structure, such as hairpins or loops. The methods and kits disclosed herein may further comprise a plurality of target-specific primers having minimal cross-hybridization to non-specific sequences present in a sample.

The target-specific primers disclosed herein may be used for efficient amplification of short nucleic acid fragments, such nucleic acids derived from FFPE samples, cell free DNA (cfDNA), cell free tumor DNA (ctDNA) and cell free fetal DNA (cffDNA). The short nucleic acid fragments can be less than about 40 bases, 50 bases, 60 bases, 70 bases, 80 bases, 90 bases, 100 bases or 120 bases. The method discloses herein may also be used for the detection and quantification of minority mutations lower than 1%, such as T790M mutation related to drug resistance in lung cancer.

Methods disclosed herein produce an amplification product that can be sequenced by next-generation sequencing platforms. Next-generation sequencing is referred to non-sanger based massively parallel DNA nucleic acid sequencing technologies that can sequence tens of thousands of, or millions to billions of DNA strands in parallel. Examples of current state of state-of-art next-generation sequencing technologies and platforms are Illumina platforms (reversible dye-terminator sequencing), 454 pyrosequencing, Ion Semiconductor sequencing (Ion Torrent), PacBio SMRT sequencing, Qiagen GeneReader sequencing technology, and Oxoford Nanopore sequencing. The present disclosure is not limited to these next-generation sequencing technologies examples. In another aspect, the methods disclosed herein can be used in a multiplex fashion when amplifying more than two targets. The methods disclosed herein are not limited to any number of multiplexing.

EXAMPLES

Example 1

Multiplex Amplification with Methylation-Modified Primers for Identification of Variants (Approach 1)

Materials and Methods

Human DNA was extracted by Qiagen DNA extraction kit according to the manufacturer's instructions and the quantity of DNA was measured both by NanoDrop (ThermoFisher, USA) and Qubit 3 (ThermoFisher, USA).

Three oncogenes were selected for this experiment. Methylation-modified forward and reverse primers were designed for detection of variants for EGFR, KIT, and TP53 oncogenes. Each primer consisted of a target-specific region and a methylation-modified auxiliary universal region.

Multiplex PCR was performed applying 6 methylation-modified primers in presence of genomic DNA, DNA polymerase, dNTP and PCR buffer in a 20 µl reaction volume. The PCR conditions consisted of initiation at 98° C. for 30 sec, 15 cycles of 98° C. 10 sec, 63° C. 4 min, 72° C. 20 sec and final extension at 72° C. 2 min.

Exonuclease I (NEB, USA) digestion to remove redundant primers and SPRIselect (Beckman Coulter, USA) beads purification to select large fragments was performed on the amplified product according to the manufacturer's instructions.

The PCR products were digested in separate reactions with either MspJI or LpnPI (NEB, USA) according to the manufacturer's instructions. The digested products were purified by SPRIselect (Beckman Coulter, USA) beads.

The digested products were ligated to adapters containing complementary sticky ends using Instant Sticky-end Ligase Master Mix (NEB, USA) according to manufacturer's instructions. The procedures were performed on an Applied Biosystems Veriti thermal cycler (ThermoFisher, USA).

The ligated DNA products were purified by SPRIselect (Beckman Coulter, USA) beads to remove surplus ligation adapters.

PCR was performed on ligated products using barcoded universal primers, hybridizing to ligated product universal priming site in presence of DNA polymerase, dNTP and PCR buffer in 20 µl reaction volume. The PCR conditions consisted of initiation at 98° C. for 30 sec, 21 cycles of 98° C. 10 sec, 68° C. 30 sec, 72° C. 20 sec and final extension at 72° C. 2 min.

The amplified products was digested with Exonuclease I (NEB, USA) to remove redundant primers and was purified by SPRIselect beads (Beckman Coulter, USA), and was then measured on a Qubit 3 (ThermoFisher, USA). The final products were sequenced bidirectionally by Sanger sequencing.

Example 2

Cancer Gene Panel for Identification of Mutations and Fusion Genes in Lung Cancer from FFPE Samples
Materials and Methods Human genomic DNA was used for this experiment to analyze possible mutations that can affect the treatment regimen.

The DNA was extracted by Qiagen DNA extraction kit according to the manufacturer's instructions and the quantity of DNA was measured both by NanoDrop (ThermoFisher, USA) and Qubit 3 (ThermoFisher, USA).

Cancer gene and primer design: based on literature search, 15 cancer related genes were selected: AKT1, ALK, BRAF, CTNNB1, EGFR, ERBB2, HRAS, KIT, KRAS, MAP2K1, MET, NRAS, PDGFRA, PIK3CA and TP53. For detection of hotspot mutations on these genes, 61 pairs of forward and reverse primers were designed for multiplex amplification of target nucleic acids.

Multiplex PCR was performed applying 122 target-specific primers containing a universal auxiliary sequence in the presence of genomic DNA, DNA polymerase, dNTP and PCR buffer in a 20 µl reaction volume. The PCR conditions consisted of initiation at 98° C. for 30 sec, 10 cycles of 98° C. 10 sec, 63° C. 4 min, 72° C. 20 sec and final extension at 72° C. 2 min.

The amplified product from the first amplification was subjected to exonuclease I (NEB, USA) treatment to remove redundant primers according to the manufacturer's instructions. Then, the resulting first amplicon was purified by SPRIselect beads (Beckman Coulter, USA).

Amplification was performed using a portion of the purified product from the first amplification and methylated universal auxiliary primers in the presence of DNA polymerase, dNTP and PCR buffer in a 20 µl reaction volume. The PCR conditions consisted of initiation at 98° C. for 30 sec, 15 cycles of 98° C. 10 sec, 69° C. 30 sec, 72° C. 30 sec and final extension at 72° C. 2 min.

Exonuclease I (NEB, USA) digestion to remove redundant primers and SPRIselect beads (Beckman Coulter, USA) purification to select large fragments was performed on the amplified product according to the manufacturer's instructions.

The amplified product was digested using either MspJI or LpnPI (NEB, USA) according to the manufacturer's instructions and was then purified by SPRIselect beads.

The digested products were ligated to adapters containing complementary sticky ends using Instant Sticky-end Ligase Master Mix (NEB, USA) according to manufacturer's instructions. The procedures were performed on an Applied Biosystems Veriti thermal cycler (ThermoFisher, USA).

The ligated DNA products were then purified by SPRIselect beads to remove surplus ligation adapters.

PCR was performed on ligated products using barcoded universal primers, hybridizing to ligated product universal priming site in presence of DNA polymerase, dNTP and PCR buffer in 20 µl reaction volume. The PCR conditions consisted of initiation at 98° C. for 30 sec, 21 cycles of 98° C. 10 sec, 68° C. 30 sec, 72° C. 20 sec and final extension at 72° C. 2 min.

The amplified products was digested with Exonuclease I (NEB, USA) to remove redundant primers and was purified with SPRIselect beads, and was then measured on a Qubit 3 (ThermoFisher, USA).

Sequencing of the libraries were performed on a MiniSeq sequencing system (Illumina, CA, USA) using MiniSeq Mid Output Kit.

The sequence data generated from the above experiment was analyzed for mutations and variations.

The methodologies and the various embodiments thereof described herein are exemplary. Various other embodiments of the methodologies described herein are possible.

Now, therefore, the following is claimed:

1. A method of enriching nucleic acid target sequences in a sample, comprising the steps of:
   in a test reaction, hybridizing two or more target-specific primers to target sequences in the sample, wherein the target-specific primers comprise a methylated universal auxiliary portion with a methylation-dependent endonuclease restriction enzyme recognition site and a target-specific portion configured to target the nucleic acid target sequences in the sample;
   subjecting the test reaction to amplification under optimal amplification conditions to produce an amplified product comprising an amplicon;
   subjecting the amplified product to digestion with a methylation-dependent endonuclease restriction enzyme to form a digestion product, wherein the digestion product comprises amplicons comprising sticky ends on each end of the strands;
   performing size selection purification on the digestion product for removal of digested primer-dimers and unused primers to produce digested amplicons comprising dsDNA;
   ligating universal adapters to dsDNA from the digested amplicons to form a ligation product, wherein the ligation universal adapters comprise a universal sequence portion and sticky ends; and
   subjecting the ligation product to amplification with barcoded universal primers complementary to a sequence on the ligating universal adapters to form a final amplification product comprising final amplicons.

2. The method of claim 1, further comprising at least one additional set of target-specific primers in at least one additional test reaction.

3. The method of claim 1, wherein the sample comprises genomic DNA.

4. The method of claim 1, wherein the sample comprises RNA and further comprising the step of, prior to first amplification, subjecting the RNA to a reverse transcription reaction to generate double-stranded cDNA.

5. The method of claim 1, wherein the method further comprises the step of subjecting the final amplicons to next-generation sequencing to generate sequence data.

6. The method of claim 5, further comprising the step of measuring allele counts at polymorphic sites in the sequence data.

7. The method of claim 1, wherein the ligation universal adapters further comprise a barcode sequence.

8. The method of claim 1, wherein the sample comprises nucleic acid selected from the group consisting of: a mixture of maternal cfDNA and cffDNA obtained from a pregnant subject, circulating cfDNA and circulating ctDNA.

9. The method of claim 1, wherein the target-specific primers comprise at least one pair of forward target-specific primers and reverse target-specific primers.

10. The method of claim 1, wherein the target sequences comprise one or more mutations that are associated with disease, cancer, disorders, infections, pharmacogenetic drug treatment (companion diagnostic), drug resistance or drug antibiotic resistance, or aneuploidy or trisomy in a gestating fetus.

11. A method of enriching nucleic acid target sequences in a sample, comprising the steps of:
   in a test reaction, hybridizing two or more target-specific primers to nucleic acid target sequences, wherein the target-specific primers comprise a complementary universal auxiliary portion at the 5'-end and a target-specific portion configured to target the nucleic acid target sequences in the sample;
   subjecting the test reaction to a first amplification with universal auxiliary primers under optimal amplification conditions to form an amplified product;

subjecting a portion of the amplified product to a second amplification using a methylated universal auxiliary primer to form a second amplified product, wherein the methylated universal auxiliary primer comprises a restriction enzyme recognition sequence;

subjecting the second amplified product to digestion with a methylation-dependent endonuclease restriction enzyme to form a digestion product comprising amplicons comprising sticky ends on each end of the strands;

performing size selection purification on the digestion product to remove digested primer-dimers and unused primers to form digested amplicons comprising dsDNA;

ligating universal adapters to dsDNA from the digested amplicons to form a ligated product, wherein the ligating universal adaptors comprise complementary sticky ends and a universal sequence portion; and subjecting the ligated product to a third amplification using barcoded universal primers complementary to sequences on the ligating universal adapters to form a final amplification product comprising final amplicons.

12. The method of claim 11, further comprising at least one additional set of target-specific primers in at least one additional test reaction.

13. The method of claim 11, wherein the sample comprises genomic DNA.

14. The method of claim 11, wherein the sample comprises RNA and wherein the method further comprises, prior to the first amplification, subjecting the RNA to a reverse transcription reaction to generate double-stranded cDNA.

15. The method of claim 11, wherein the method further comprises the step of subjecting the final amplicons to next-generation sequencing to generate sequence data.

16. The method of claim 15, further comprising the step of measuring allele counts at polymorphic sites in the sequence data.

17. The method of claim 11, wherein the ligation universal adapters further comprise a barcode sequence.

18. The method of claim 11, wherein the sample comprises nucleic acid selected from the group consisting of: a mixture of maternal cfDNA and cffDNA obtained from a pregnant subject, circulating cfDNA and circulating ctDNA.

19. The method of claim 11, wherein the target-specific primers comprise at least one pair of forward target-specific primers and reverse target-specific primers.

20. The method of claim 11, wherein the target sequences comprise one or more mutations that are associated with disease, cancer, disorders, infections, pharmacogenetic drug treatment (companion diagnostic), drug resistance or drug antibiotic resistance, or aneuploidy or trisomy in a gestating fetus.

* * * * *

SEQUENCE LISTING

<160> NUMBER OF SEQ ID NOS: 10

<210> SEQ ID NO 1
<211> LENGTH: 70
<212> TYPE: DNA
<213> ORGANISM: Homo sapiens

<400> SEQUENCE: 1
aatgatacgg cgaccaccga gatctacaca atacgccaca ctctttccct acacgacgct     60
cttccgatct 70

<210> SEQ ID NO 2
<211> LENGTH: 114
<212> TYPE: DNA
<213> ORGANISM: Homo sapiens

<400> SEQUENCE: 2
gaagctccca accaagctct cttgaggatc ttgaaggaaa ctgaattcaa aaagatcaaa    60
gtgctgggct ccggtgcgtt cggcacggtg tataaggtaa ggtccctggc acag          114

<210> SEQ ID NO 3
<211> LENGTH: 66
<212> TYPE: DNA
<213> ORGANISM: Homo sapiens

<400> SEQUENCE: 3
agatcggaag agcacacgtc tgaactccag tcacggcgta ttatctcgta tgccgtcttc    60
tgcttg                                                                66

<210> SEQ ID NO 4
<211> LENGTH: 66
<212> TYPE: DNA
<213> ORGANISM: Homo sapiens

<400> SEQUENCE: 4
caagcagaag acggcatacg agataatacg ccgtgactgg agttcagacg tgtgctcttc    60
cgatct                                                                66

<210> SEQ ID NO 5
<211> LENGTH: 114
<212> TYPE: DNA
<213> ORGANISM: Homo sapiens

<400> SEQUENCE: 5
ctgtgccagg gaccttacct tatacaccgt gccgaacgca ccggagccca gcactttgat    60 cttttgaat tcagtttcct tcaagatcct caagagagct tggttgggag cttc            114

<210> SEQ ID NO 6
<211> LENGTH: 70
<212> TYPE: DNA
<213> ORGANISM: Homo sapiens

<400> SEQUENCE: 6
agatcggaag agcgtcgtgt agggaaagag tgtggcgtat tgtgtagatc tcggtggtcg    60
ccgtatcatt                                                            70

<210> SEQ ID NO 7
<211> LENGTH: 119
<212> TYPE: DNA
<213> ORGANISM: Homo sapiens

<400> SEQUENCE: 7
tcctgacctg gagtcttcca gtgtgatgat ggtgaggatg ggcctccggt tcatgccgcc    60
catgcaggaa ctgttacaca tgtagttgta gtggatggtg gtacagtcag agccaacct     119

<210> SEQ ID NO 8
<211> LENGTH: 119
<212> TYPE: DNA
<213> ORGANISM: Homo sapiens

```
<400> SEQUENCE: 8
aggttggctc tgactgtacc accatccact acaactacat gtgtaacagt tcctgcatgg      60
gcggcatgaa ccggaggccc atcctcacca tcatcacact ggaagactcc aggtcagga     119

<210> SEQ ID NO 9
<211> LENGTH: 156
<212> TYPE: DNA
<213> ORGANISM: Homo sapiens

<400> SEQUENCE: 9
cctccaacct aatagtgtat tcacagagac ttggcagcca gaaatatcct ccttactcat      60
ggtcggatca caaagatttg tgattttggt ctagccagag acatcaagaa tgattctaat     120
tatgtggtta aaggaaacgt gagtacccat tctctg                              156

<210> SEQ ID NO 10
<211> LENGTH: 155
<212> TYPE: DNA
<213> ORGANISM: Homo sapiens

<400> SEQUENCE: 10
agagaatggg tactcacgtt tcctttaacc acataattag aatcattctt gatgtctctg      60
gctagaccaa aatcacaaat ctttgtgatc cgaccatgag taaggaggat atttctggct     120
gccaagtctc tgtgaataca ctattaggtt ggagg                               155
```